United States Patent [19]
Hoffmann

[11] Patent Number: 5,859,922
[45] Date of Patent: Jan. 12, 1999

[54] PROCESS OF DETERMINING THE THREE-DIMENSIONAL LOCATION OF A PACEMAKER LEADS IN THE HEART OF A SUBJECT

[76] Inventor: Kenneth R. Hoffmann, 4204 Charleston Rd., Matteson, Ill. 60443

[21] Appl. No.: 805,074

[22] Filed: Feb. 21, 1997

[51] Int. Cl.⁶ ..................................................... G06K 9/00
[52] U.S. Cl. ............................ 382/128; 382/154; 607/27
[58] Field of Search ..................................... 382/128, 130, 382/131, 132, 154, 294; 600/424; 607/27; 128/922

[56] References Cited

U.S. PATENT DOCUMENTS

| | | | |
|---|---|---|---|
| 5,282,254 | 1/1994 | Chiu et al. | 382/6 |
| 5,285,786 | 2/1994 | Fujii | 128/653.1 |
| 5,435,310 | 7/1995 | Sheehan et al. | 128/653.1 |
| 5,570,430 | 10/1996 | Sheehan et al. | 382/128 |
| 5,734,739 | 3/1998 | Sheehan et al. | 382/128 |
| 5,758,645 | 6/1998 | Qian | 128/653.01 |

*Primary Examiner*—Andrew W. Johns
*Attorney, Agent, or Firm*—Rockey, Milnamow & Katz, Ltd.

[57] ABSTRACT

A process of determining the three-dimensional location of a pacemaker lead in the heart of a subject is provided. The process includes the steps of acquiring a plurality of two-dimensional images of the lead; calculating the imaging geometry; identifying the two-dimensional position of the lead in each of the images; temporally interpolating the identified two-dimensional positions to identify a two-dimensional position of image at a single time; and calculating the three dimensional location of the lead from the two-dimensional position at that time.

16 Claims, 4 Drawing Sheets

CENTERING PHANTOM

TOP PLATE    BOTTOM PLATE

PROCESS OF DETERMINING THE THREE-DIMENSIONAL LOCATION OF A PACEMAKER LEADS IN THE HEART OF A SUBJECT

TECHNICAL FIELD OF THE INVENTION

The field of this invention is three-dimensional imaging. More particularly, the present invention relates to a process of determining the three-dimensional location of pacemaker leads in the heart of a subject.

BACKGROUND OF THE INVENTION

An estimated one million people in the United States have pacemaker implants. Although pacemakers are being placed in younger populations, little is known about the longevity of the leads in the pacemakers. The long term reliability of lead components is, at best, uncertain. The uncertainty can be life threatening. Several lead models using polyurethane have exhibited degradation of the insulation, resulting from environmental stress cracking. A predisposition to such insulation failure may not be recognized prior to market release. Other leads have a small metal J shape retention located beneath the outer insulation. These metal components may fracture and erode through the insulation. The protruding metal fragment can puncture the heart and has been associated with the death of two patients and pericardial tamponade in at least five others. Approximately 21,000 of these lead models have been implanted in the United States, and approximately 42,000 world wide.

Detection of the fractures is problematic: pacing and sensing may be normal, and fractures are difficult to visualize even with fluoroscopy in a cardiac catherization lab. In one study of 156 patients, 35 (22.4%) had a definite fracture. In five patients who had a irregularity in the lead contour on the initial evaluation and who underwent repeat fluoroscopy approximately one month after the initial fluoroscopy, three were identified as having a definite fracture. Neither the age of the patients, the time since lead implant, nor the site of the fracture correlated with the incidence of retention wire failure. Although fractures involving portions of the retention wire extending beyond the insulation were easy to diagnose, fractures still enclosed in the insulation were found to be extremely subtle. The ability to visualize such fractures depends on the orientation of the lead in a given view. Even with the most sensitive method available, i.e., visual evaluation fluoroscopic images obtained at high frame rates, one in eight normal leads was shown to have a fracture on follow-up. Moreover, implantable devices can develop time dependent failure modes that simply cannot be modeled in the laboratory.

Pacemaker leads exhibit relatively smooth and continuous motion. Abnormalities in the lead, such as occult fractures and perhaps insulation degradation, will likely result in distortions in the motion, which could be revealed by 3D motion analysis. In addition, if the 3D motion analysis is coupled with stress analysis, it provides an even more sensitive evaluation of the status of the lead. Because patients are being followed with frequent imaging, the monitoring and quantitation of changes in 3D motion over time may thus facilitate detection of fractures and may be useful as an indicator of the possibility of future fractures.

There are other benefits to the development, in vitro testing, and in vivo evaluations of implants. New approaches are required to advance knowledge for accelerated testing for durability and reliability of physical components. This applies to design robustness of implants to include failure modes, patient variability, biological stability, computer aided design and manufacturing. New models are needed to reduce manufacturing empiricism (trial and error) as well as to enable in vitro performance. More biostability data are needed, especially relating to the performance of implant materials under dynamic situations and addressing the severity of the biologic environment in both short and long-term use scenarios.

There is dearth of information on long-term effects of implants in humans. Thus, the scientific community is faced with two related but separate problems. One, individuals with pacemakers need to be monitored and the status of their leads need to be evaluated accurately. Two, methods need to be developed by which to develop and evaluate new models in vitro and in vivo. The essential first step toward addressing both of these problems is the development of methods for determination of the 3D motion of pacemaker leads in vivo. A determination of the 3D motion of leads in populations of patients followed over time may provide useful information regarding progression of fractures. Further, the patient data could be combined (e.g., by parameterization) so as to lead to a greater understanding of the motions in the patient population and the development of in vitro modeling that truly mimics the in vivo lead motion. The techniques used to determine the motion of the pacemaker leads can also be used to evaluate the motions generated by the testing devices.

Tomographic techniques, such as CT, MRI, or ultrasound, yield only a single slice at a given point in time, and cannot provide instantaneous 3D positions of the entire lead. With the current technology, the only means to obtain accurate 3D motion throughout the heart cycle is to use biplane image acquisition techniques. To date, only Harrigan et al. have even mentioned a technique for pacemaker lead assessment in vivo (T. Harrigan, R. Kirkeeide, S. Jalal, T. Berveridge, B. D. Montgomery, H. B. Shih: Assessment of pacing lead curvature and strain with three dimensional reconstruction of biplane cineangiographic images in vivo. JACC 27:345A, 1996). The Harrigan disclosure is only an abstract and does not teach details about how to perform such a technique. Of more relevance to the present disclosure is the fact that Harrigan makes no mention of the problem of non-synchronous image generation.

The problems associated with the effects of non-synchronous acquisitions can be minimized to some extent by limiting image generation to the diastolic phase of the cardiac cycle where cardiac motion is at a minimum. However, such limited measurements during diastole of a little consequence to studies designed to evaluate the effects of stress on the pacemaker components, which stress is likely greatest during systole. There remains a need in the art, therefore, for an accurate and precise means of determining the location and movement of pacemaker components throughout the entire cardiac cycle.

BRIEF SUMMARY OF THE INVENTION

The present invention provides a process of determining the three dimensional location of a pacemaker lead in the heart of a subject. The process includes the steps of (a) acquiring a plurality of two-dimensional images of the lead; (b) calculating the imaging geometry; (c) identifying the two-dimensional position of the lead in each of the images; (d) temporally interpolating the identified two-dimensional positions to identify a two-dimensional position of lead at a single time; and (e) calculating the three dimensional location of the lead from the two-dimensional position at that time.

In one embodiment, acquiring the images is accomplished by providing a biplane imaging system, determining the pixel size of each imaging system, obtaining at least one image of the pacemaker lead in the subject in each imaging plane and calibrating the imaging system by obtaining images of a calibration object in each imaging plane.

The biplanar imaging system has two imaging planes, which planes are not co-planar. Neither of those imaging planes is perpendicular to the plane of the pacemaker lead. One of the two planes is preferably positioned parallel to the plane of the pacemaker lead. The two imaging planes are oriented between about 30 degrees and 150 degrees relative to each other.

The imaging geometry of the system is calculated from acquired images of a calibration object using the Metz-Fencil, enhanced Metz-Fencil or single projection analysis technique. Use of the single projection technique is preferred. A plurality of images of different orientations of the calibration object can be used to enhance the accuracy and precision of the process.

The two-dimensional position of the lead in each imaging plane is determined by identifying in each image a centerline of the lead. The centerline of the lead is identified by indicating a plurality of points along the length of the lead centerline. Preferably, at least from about 20 to about 30 points are indicated. The location of those points can be done manually or automatically using, for example, template matching and vessel tracking techniques.

Temporal interpolation is accomplished by determining the correspondence of points along the lead centerline in each image and temporally interpolating those points to a particular time. The particular time chosen for temporal interpolation is the time at which any one image was obtained. The three-dimensional location of the lead is calculated using epipolar techniques.

BRIEF DESCRIPTION OF THE DRAWINGS

In the drawings that form a portion of the specification.

DETAILED DESCRIPTION OF THE INVENTION

I. Process of Locating Pacemaker Leads

The present invention provides a process of determining the three dimensional (3D) location of a pacemaker lead in the heart of a subject. The process can be carried out in situ or in vivo. The process can be used with any subject although human subjects are preferred.

Figure 1:
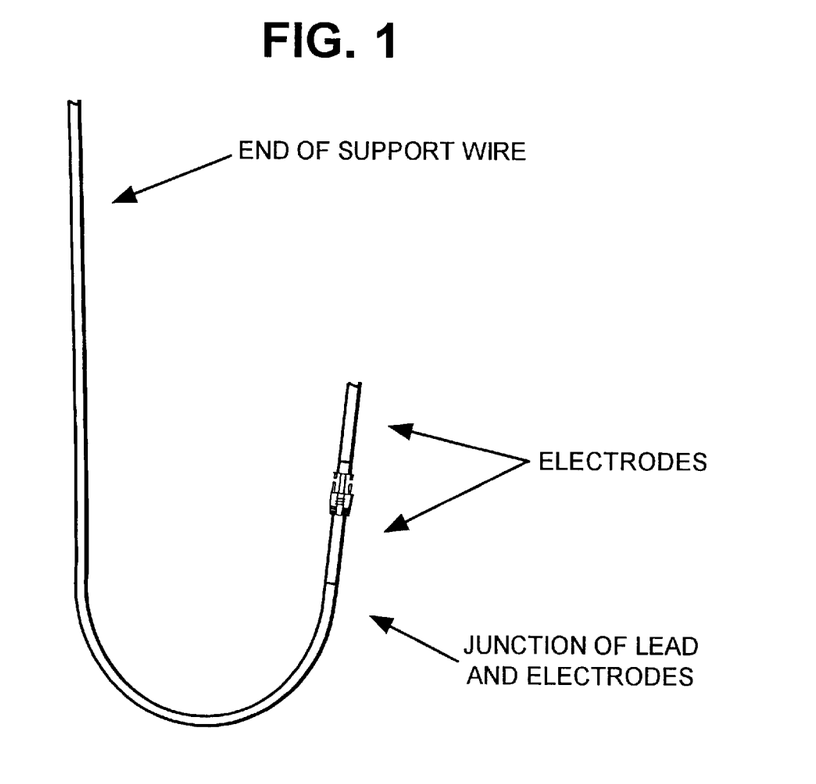
FIG. 1 is a schematic illustration of a cardiac pacemaker showing the electrode and lead components.

As is well known in the art, a pacemaker comprises electrodes and a lead, which lead is characterized by a sheath of wires surrounded by a flexible non-conductive coating (e.g., plastic)(See FIG. 1). A process of this invention can be used to locate the lead and/or electrodes at any point in time. The description to follow discloses the process as it applies to leads only. It will be readily apparent to a skilled artisan, however, how to apply the process to electrode determination either alone or in combination with lead determination. By locating the position of the lead at a plurality of times, the motion of the lead during the cardiac cycle can be obtained.

The process of the present invention includes the steps of acquiring a plurality of two-dimensional images, calculating the imaging geometry employed, identifying the lead positions in each two-dimensional image, temporally interpolating the image data, and calculating the 3D position(s) from the known geometry using epipolar techniques.

A. Acquisition of Images

A plurality of two-dimensional images are obtained from the subject in two different imaging planes. The acquisition of the images thus uses an imaging system in which more than two planar projections can be obtained. Such a system can be a biplanar system as described below or a movable single plane system. The imaging medium can be x-rays (in situ or in vivo use) or video camera imaging systems (in situ use).

The imaging geometry of each system is adjusted so that all portions of the lead to be evaluated (approximately three inches proximal to the distal electrodes) are visible in each image plane throughout the heart cycle. A plurality of images are obtained in each image plane. Images are obtained alternately in each image plane. The total number of images obtained is a function of the rate of image taking and the duration of the cardiac cycle. The duration of image taking should encompass at least one complete cardiac cycle (diastole and systole). Preferably, the duration of image taking should encompass two or more cardiac cycles. The only limit in duration is exposure of the subject to X-rays: there is no duration limit when using video imaging. The frequency of image taking is limited only by the means of data conversion used to collect and analyze the image data. Where digitalization is used, the limit of image frequency is one image every 1/60th of a second. In accordance with this embodiment, an image is taken in each image plane every 1/30th of a second. The greater the duration and frequency of image taking, the greater the accuracy and precision of the calculated three-dimensional position.

1. Biplanar Imaging System

Figure 2:
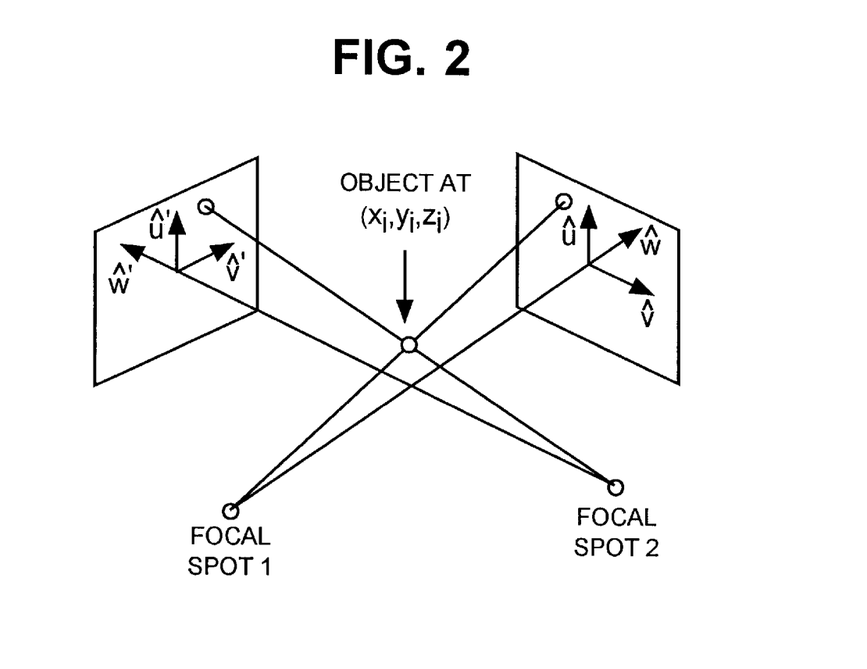
FIG. 2 is a schematic illustration of a biplanar imaging system showing two focal points and two imaging planes.

A schematic illustration of a biplane imaging system using X-rays is shown in FIG. 2. As shown in FIG. 2, the system includes two focal spots (origin of X-rays) and two corresponding imaging planes, aligned with the focal points such that X-rays pass through the lead in the subject heart and generate an image in the respective plane. The dual projection imaging system is defined by the location of the focal spots relative to each other and the distances between the focal spots and their respective imaging planes, called the source to imaging distance (SID).

For best results, the two image planes are defined by a particular spatial orientation to each other and to the lead to be imaged. First, neither image plane should be positioned perpendicular to the plane of the pacemaker lead. Preferably, one of the image planes is about parallel to the plane of the pacemaker lead. Second, the two image planes are not-coplanar (i.e., they are not in the same plane). The accuracy and precision of the present process can be enhanced by positioning the image planes at an angle of between 30 and 150 degrees to each other. In a preferred embodiment, the two image planes are positioned at an angle of between 60 and 120 degrees to each other. More preferably, the angle between the image planes is about 90 degrees. The data from each generated image is digitized and stored in a retrievable data storage means such as a computer.

2. Characterization of the Imaging System

The imaging system should be checked periodically to measure and correct for geometric distortions and to determine the pixel size of each imaging system. Preferably, the imaging system is characterized at least once a week. Even more preferably, the system is characterized immediately prior to subject imaging. Typically, the imaging system is characterized by acquiring images of a phantom wire mesh similar to that used for contact testing of cassettes. The wire mesh phantom is placed on the grid of the image intensifier associated with one of the image planes. The mesh phantom is oriented such that the wires run approximately parallel to the horizontal axis of the image intensifier. Digital images are acquired for each of the fields of view that are to be used for patient acquisitions. Using the known rectilinear relationship of the wire mesh, the extent and correction can be determined using techniques well known in the art (See, e.g., K. R. Hoffmann, Y. Chen, J. Esthappan, S. Y. Chen, J. D. Carroll, "Pincushion correction techniques and their effects on calculated 3D positions and imaging geometries," *Proc. SPIE* 2710: 462–467, 1996). The known distances between the wires combined with the distances measured in the images is used to determine the pixel size, i.e., the number of cm/pixel, in the image.

Figure 3:
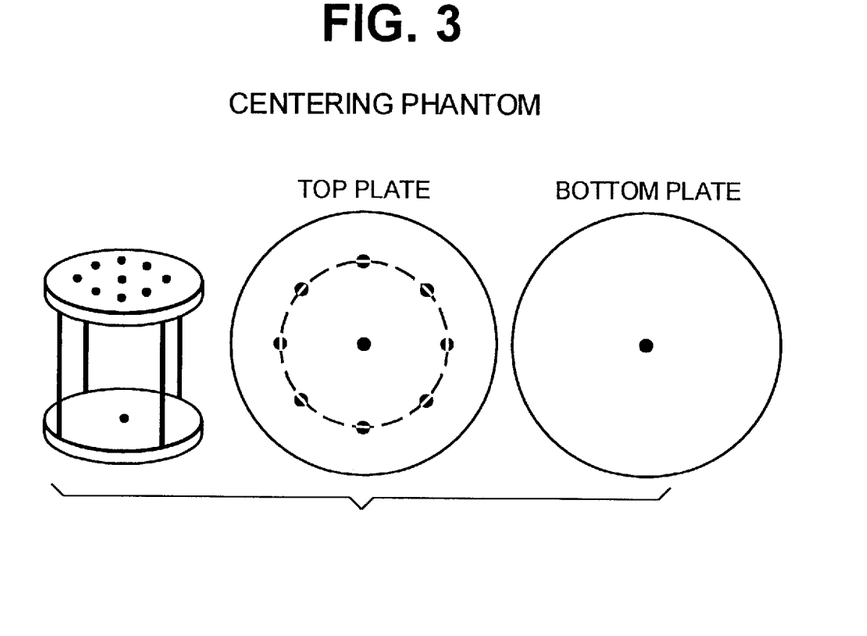
FIG. 3 is a schematic illustration of a centering phantom used to characterize an imaging system.

FIG. 3 shows an exemplary and preferred centering phantom that can be used to characterize the imaging system. This phantom consists of two disks of Lucite, approximately ¼ inch thick and having a diameter of approximately 10 cm. These disks are connected ridgidly either by a Lucite tube, or Lucite or aluminum rods approximately 20 cm in height. These supports are stable and allow less than 0.2 degree deviation from parallel for the two disks. The two disks must be parallel to each other to within 0.2 degrees. In the top disk, a 1 mm diameter ball bearing (e.g., lead shot) is placed at the center of the disk with a tolerance of 0.1 mm. At a radius of 3 cm, 8 other 1 mm ball bearings are placed, preferably at uniform intervals along the circle, with a tolerance of 0.1 mm. In the bottom disk, a 1 mm diameter ball bearing is placed at the center of the disk, with a tolerance of 0.1 mm. The center ball bearings of the two disks must align to within 0.1 mm. The vertical separation of the ball bearing centers should be known to 0.5 mm or better.

As described in detail hereinafter, the origin of the image coordinate system for a typical imaging system is fixed and corresponds to a point in the image plane. The origin is taken to be the point at which a perpendicular line from the corresponding focal spot intersects the image plane. The images of the phantom are analyzed to determine the origin of the acquired images obtained. The image of the lead shot can be indicated manually. The local background trend is estimated and subtracted. Region growing can be employed to identify the central region of the image of the lead shot using a threshold lying halfway between the background level and the maximum intensity in the lead shot region. The center of mass of the grown region is taken as the origin of the lead shot and thus the image. The positions of the off-center beads is used to calculate a second estimate of the center, and can be used as a precision measure of the center. Using these techniques, the point of origin in the system can be estimated to within about one pixel (approximately 0.3 mm). To a first order, the error in the position of the origin translate into errors in the angles between the imaging systems. Thus, a 0.3 mm error results in a $3*10^{-5}$ radian error for an SID of 100 cm.

B. Determination of Imaging Geometry

After acquiring and storing the subject images, the imaging geometry is determined. The phrase "imaging geometry" refers, as is well known in the imaging art, to the spatial relationships between the various components of the imaging system. Those components include the relative and absolute locations of (1) the focal points, (2) the object to be imaged and (3) the image or projection planes. Knowledge of the imaging geometry is a necessary prerequisite to conversion of two-dimensional images in the two different image planes to an actual three-dimensional location of the imaged object in space.

Figure 4:
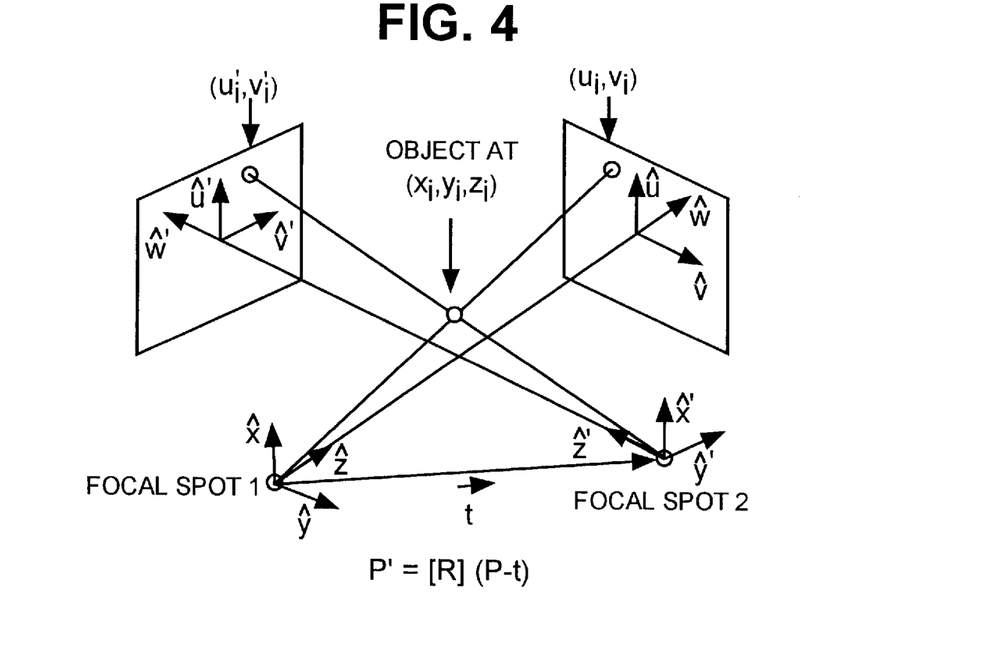
FIG. 4 is a schematic illustration of the coordinate systems of a biplanar imaging system.

The coordinate systems of a representative biplanar imaging system are schematically shown in FIG. 4. As shown in FIG. 4, the system comprises a first and a second imaging system. Each system is characterized by its own coordinate system. By way of example, the first system of FIG. 4 is characterized by a set of coordinates having a point of origin at the first focal point. That coordinate system is designated (x, y, z), with the corresponding unit vectors designated ($\hat{x}$, $\hat{y}$, $\hat{z}$). The projected image of the object in that first system has coordinates designated (u, v, w), with the corresponding unit vectors designated ($\hat{u}$, $\hat{v}$, $\hat{w}$). The vectors, u, v, and w are parallel to the vectors, x, y, and z; u and v lie in the first image plane. In that first coordinate system, the location of a particular point (i) in the object to be imaged (e.g., pacemaker lead) is designated ($x_i$, $y_i$, $z_i$).

The second system of FIG. 4 is similarly characterized by a second set of coordinates having a point of origin at the second focal point. That coordinate system is designated (x', y', z'), with the corresponding unit vectors ($\hat{x}'$, $\hat{y}'$, $\hat{z}'$). The projected image of the object in that second system has coordinates designated (u', v', w') ), with the corresponding unit vectors ($\hat{u}'$, $\hat{v}'$, $\hat{w}'$). The vectors, u', v', and w' are parallel to the vectors, x', y', and z'; u' and v' lie in the second image plane. In that second coordinate system, the location of a particular point (i) in the object to be imaged (e.g., pacemaker lead) is designated ($x'_i$, $y''_i$, $z''_i$).

The location of a particular point in one system (e.g., the first imaging system) can be converted to a corresponding point in the other (e.g., second) system by a matrix transformation according to Equation (1), below $$\begin{bmatrix} x_i' \\ y_i' \\ z_i' \end{bmatrix} = \begin{bmatrix} r_{11} & r_{12} & r_{13} \\ r_{21} & r_{22} & r_{23} \\ r_{31} & r_{32} & r_{33} \end{bmatrix} \left\{ \begin{bmatrix} x_i \\ y_i \\ z_i \end{bmatrix} - \begin{bmatrix} t_x \\ t_y \\ t_z \end{bmatrix} \right\}, \quad (1)$$

i.e., $P^{\perp'}_i = [R](P^{\perp}_i - t^{\perp})$, where $P^{\perp}_i = (x_i, y_i, z_i)$ and $P^{\perp'}_i = (x'_i, y'_i, z'_i)$ and where the terms $r_{k1}$ are the elements of the orthogonal matrix [R] with rows $\hat{r}_k$ that describes rigid rotation of the x'y'z' axes into the xyz axes, and where $t_x$, $t_y$, and $t_z$ are the elements of the vector t that describes, in the xyz system, the 3D translation from the origin of the xyz system to the origin of the x'y'z'system (i.e., from the position of the focal spot used for the first view to that used for the second view). The predominant function of determining the imaging geometry is to accurately and precisely define the values of [R] and t for the particular imaging system being used.

To accurately and precisely define the various parameters ([R] and t) of the imaging geometry, it is necessary to acquire images of an object that has a plurality of well defined, multi-planar detectable points. From the knowledge of the precise location of those points together with the acquired images of those points, a calibration image can be obtained and the geometrical parameters of the system calculated. In certain circumstances, the object to be imaged contains a sufficient number of such points. In this circumstance, the object per se can thus serve as a calibration object. Indeed, techniques for determining imaging geometry without the use of secondary calibration objects are known in the art. Typically, however, conventional pacemakers do not contain a sufficient number of such calibration points. Therefore, for best results, use of an external or secondary calibration object is preferred.

Techniques for calculating the imaging geometry of a biplanar imaging system with the use of an external calibration object are well know in the art. Exemplary such techniques are those described by Potel et al. (M. J. Potel, J. M. Rubin, S. A. MacKay, A. M. Aisen, J. Al-Sadir, and R. E. Sayre, "Methods for evaluating cardiac wall motion in three dimensions using bifurcation points of the coronary arterial tree," Invest Radiol 8: 47–57, 1983), the Metz-Fencil technique (See, e.g., C. E. Metz and L. E. Fencil, "Determination of three-dimensional structure in biplane radiography without prior knowledge of the relationship between the two views," Med Phys 16: 45–51, 1989; L. E. Fencil and C. E. Metz, "Propagation and reduction of error in three-dimensional structure determined from biplane views of unknown orientations," Med Phys 17: 951–961, 1990) and the enhanced Metz-Fencil technique (K. R. Hoffmann, C. E. Metz, and Y. Chen, "Determination of 3D imaging geometry and object configurations from two biplane views: an enhancement of the Metz-Fencil technique." Med Phys 22: 1219–1227, 1995).

Figure 5:
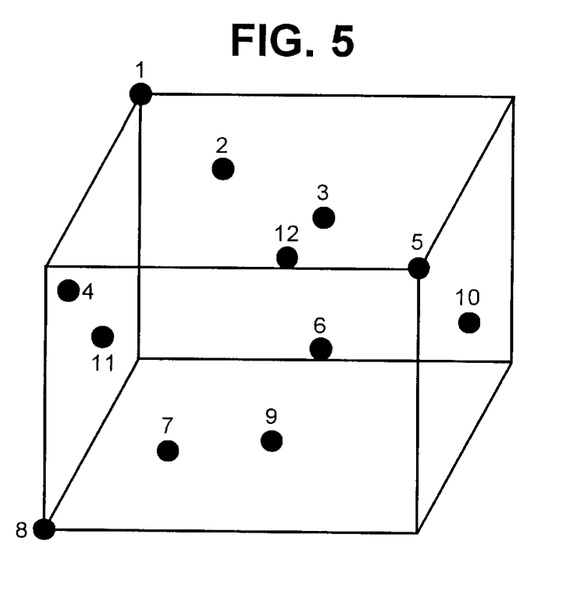
FIG. 5 is a schematic illustration of a calibration object used to determine imaging geometry.

1. Calibration Acquisition

Where a calibration object is used, images of that object in the two image planes are obtained subsequent to the acquisition of the subject images. The calibration object comprises at least four detectable points, positioned in space so that the four points define at least two planes (e.g., at least one of the four points is not co-planar with the other points). Preferably, the calibration object contains more than four points. The accuracy and precision of measurement increase with the number of detected points in the calibration object. An exemplary calibration object is shown in FIG. 5. The calibration object of FIG. 5 is a cube made of a non-detectable substance (e.g., plastic), which cube contains a plurality of detectable points (e.g., radio-opaque beads). The location of each of the points is known both in absolute terms and in relative terms (relative to each other). By way of example, twelve lead beads are distributed among three corners, the center of three faces, and along the diagonals and off-center on three faces. After acquisition of images from the subject, the subject is removed from the imaging system and the calibration object is placed in the system such that most of the detectable points can be imaged in each image plane. Images of the object are then obtained: at least one image in each plane is required. The images acquired for the phantom are used to determine the imaging geometry used for the patient and to assess the reliability of the calculated imaging geometry.

Calculation of the imaging geometry requires calibration of the imaging system, determination of uniquely identifiable points on the calibration object, indication of those points in the images of the calibration object, and determination of the imaging geometry using those points and the SIDs. The correspondence between points in each of the biplane images of the calibration phantom and the lead beads in the phantom are determined by examining the acquired images and comparing them with various hand-held orientations of the calibration phantom. To improve the accuracy of the image positions of the lead beads, the pixel with the locally maximum pixel value is found automatically, the average pixel value in a 5×5 pixel region about this maximum is calculated, and the center of mass is calculated from those pixels with pixel values above this average value.

As set forth above, any of the Potel, Metz-Fencil or enhanced Metz-Fencil techniques can be used for calculating the image geography from the acquired images of the calibration object. Another technique, the single projection technique takes additional a priori information into account (K. R. Hoffmann, J. Esthappan, S. Li, C. Pelizzari, "A simple technique for calibrating imaging geometries," Proc. SPIE 2708: 371–376, 1996). It is this method that is preferably used in the process of the present invention. After determination of the position of the phantom relative to the focal spot for each projection, the Procrustes technique is used to calculation the rotation and translation matrices relating the two x-ray imaging systems.

2. The Single Projection Technique

Figure 6:
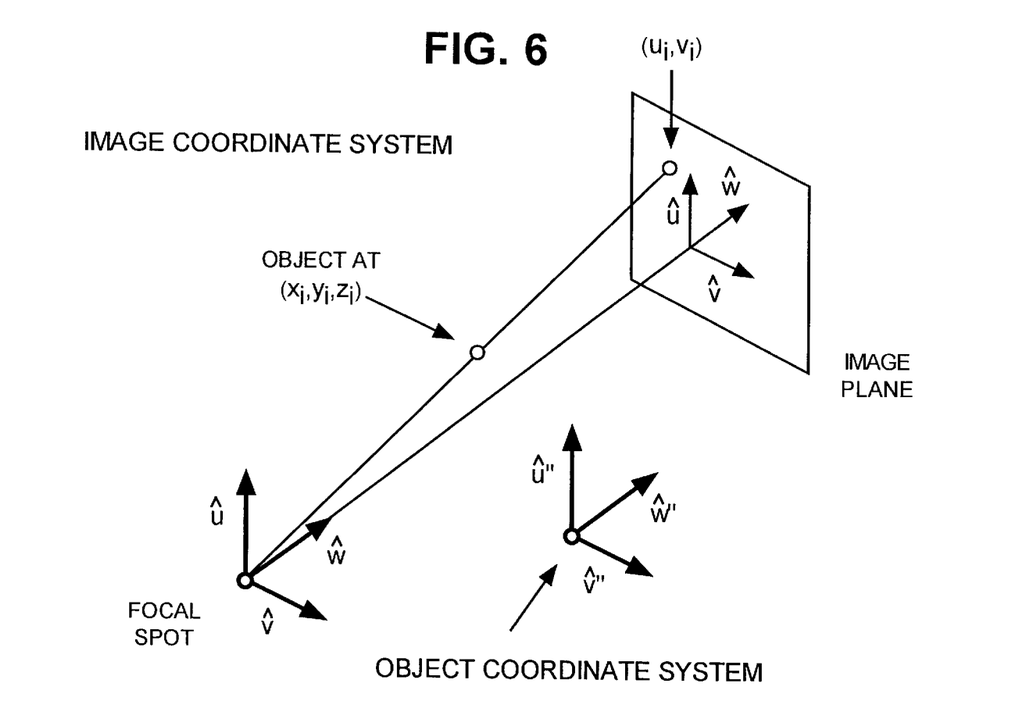
FIG. 6 is a schematic illustration of the single projection technique for calculating imaging geometry.

The basic concepts of the single projection technique are shown in FIG. 6. As set forth above, a 3D imaging coordinate system, xyz, is defined such that its origin is located at the focal spot used for a particular view, and its axes are specified by the unit vectors $\hat{x}$, $\hat{y}$, and $\hat{z}$. An image plane is located at a distance D from the focal spot, and vectors u, v, and w are defined parallel to the vectors, x, y, and z, respectively, with u and v lying in the image plane and with w and z perpendicular to the image plane. When an image of an object consisting of a number of identifiable points is obtained with this imaging system, the image coordinates $(u_i, v_i)_T$ of the projection of the i-th point in the image plane is related to the 3D position of that point, $(P_i)_T=(x_i, y_i, z_i)_T$ by Equations (1a) and (1b), below $$(u_i)_T = (x_i)_T * D/(z_i)_T \tag{1a}$$

and $$(v_i)_T = (y_i)_T * D/(z_i)_T, \tag{1b}$$

where the subscript "T" implies that these are the "true" positions, as opposed to measured positions which are indicated with the subscript "M". The measured image coordinates $(u_i)_M$ and $(v_i)_M$ contain errors arising from pixelation, noise in the image data, and the techniques used for determining their location.

Independent of the imaging system, a coordinate system can be defined relative to points in the object itself. The "object" coordinate system is denoted by x", y", z" (See FIG. 6). The position of the i-th point in the "object" coordinate system is defined as $P''_i$, where $P''_i=(x''_i, y''_i, z''_i)$ and is related to its position in the "imaging" coordinate system, $P_i$, by the transformation of Equation (2), below $$P_i = [R]^T P''_i + t, \tag{2}$$

where $[R]^T$ is a rotation matrix and t is a translation vector relating the origins of the primed and unprimed coordinate systems.

a. The Linear Solution

By combining equations (1) and (2), a set of equations can be derived relating the image data and the coordinates of the object points in the object coordinate system. These equations are similar to those presented as eqs. (1), (2), and (7) by Metz and Fencil (L. E. Fencil and C. E. Metz, "Propagation and reduction of error in three-dimensional structure determined from biplane views of unknown orientations," Med Phys 17: 951–961, 1990). The calculation of [R] and t follows the method derived in their paper, except that in their equation (14b), the $\xi,\eta,1$, is replaced respectively by x", y", z" defined herein. As in the Metz-Fencil method, the linear solution results in two rotation matrices and in a unit translation vector, $\hat{t}'$. The magnitude of the translation vector, $|t|$, is given by the Equation 3, below $$|t| = \frac{\sum_i [(\hat{\xi}_i \cdot \hat{t})(\hat{\xi}_i \cdot [R]^T P''_i) - (\hat{t} \cdot [R]^T P''_i)]}{\sum_i [1 - |\hat{\xi}_i \cdot \hat{t}|^2]} \tag{3}$$

where the summations ($\Sigma$) are over all the corresponding points, and $\hat{\xi}_i = [u_i/D, v_i/D, 1]^T$. As in the Metz-Fencil technique, there are four possible solutions, arising from the two rotation matrices and the sign ambiguity of t. Two of these solutions yield $t_z < 0$, which effectively places the object behind the focal spot, and can thus be eliminated. Of the other two that place the object in front of the focal spot, one yields an object that is rotated approximately 180° about t relative to its true orientation; the other yields the object oriented "correctly" to within the effects of input error and has the smaller image error (defined below) of these latter two. Thus, by identifying the solution in front of the focal spot with the smaller image error, the solution resulting from the "correct" R-t combination is obtained. Although this modified Metz-Fencil approach can provide a good first estimate of the orientation and position, an iterative approach, based on the projection-Procrustes technique (K. R. Hoffmann, C. E. Metz, and Y. Chen, "Determination of 3D imaging geometry and object configurations from two biplane views: an enhancement of the Metz-Fencil technique." Med Phys 22: 1219–1227, 1995) provides more accurate results (see below).

b. The Iterative Refinement of [R] and t

The iterative approach proceeds as follows. After measurement of $P''_i$ and the coordinates $(u_i)_M$ and $(v_i)_M$, and by use of the relationships given in equations 1 and 2, the 3D positions of the object points in the unprimed (imaging) coordinate system are then determined in three steps: (1) an initial positioning of a model of the object and refinement of t is performed; (2) the orientation of the model is iteratively adjusted using a projection-Procrustes technique (K. R. Hoffmann, C. E. Metz, and Y. Chen, "Determination of 3D imaging geometry and object configurations from two biplane views: an enhancement of the Metz-Fencil technique." Med Phys 22: 1219–1227, 1995); and (3) Refinement of t is repeated after refinement of the orientation is complete. Steps 2 and 3 are repeated a specified number of times.

(1) Initial Adjustment of t

After [R] and t are calculated using the linear technique, the model is translated and rotated according to equation 2. The projection of the model is generated by use of the projection equations (1a) and (1b), thereby producing image data, $u_i$ and $v_i$. The differences between $(u_i)_M$ and $(v_i)_M$ and $u_i$ and $v_i$, respectively, are calculated and averaged using Equations (4a) and (4b), below $$difu = \Sigma_i ((u_i)_M - u_i) \tag{4a}$$

and $$difv = \Sigma_i ((v_i)_M - v_i), \tag{4b}$$

where the index i runs over the number of identified points in the image. The quantities difu and difv indicate the error in the center of mass of the model along the x and y axes in the imaging plane, respectively. Next, t is adjusted on the basis of these differences, according to Equations (5a) and (5b), below $$t_x = (t_x)_{prev} - difu * (t_z)_{prev}/D \tag{5a}$$

and $$t_y = (t_y)_{prev} - difv * (t_z)_{prev}/D, \tag{5b}$$

where the subscript "prev" indicates components of the previous t. The factor $(t_z)_{prev}/D$ appears because the errors must be corrected by the magnification used in the calculation of difu and difv (i.e., by the previous magnification).

For the adjustment of $t_z$, the projection-Procrustes technique, summarized briefly below, is applied. The scaling factor relating the points in the model and their projections onto the projection lines is calculated, and $t_z$ is then adjusted by this scaling factor.

(2) The Projection-Procrustes Technique

The projection-Procrustes technique rotates, translates, and scales the model so as to align the points in the model optimally, in a least squares sense, with their corresponding projection lines. For optimal alignment of the set of points with the projection lines, the sum of the squares of the distances between the reconstructed points and their respective projection lines is minimized.

The distance between a particular point and its respective line is given by Equation (6), below $$d_i = |P_i - (P_i)_p|, \tag{6}$$

where $(P_i)_p$ is the projection of $P_i$ onto its respective projection line. This projection is given by Equation (7), below $$(P_i)_p = [P_i \cdot \hat{h}_i]\hat{h}_i \tag{7}$$

where $\hat{h}_i = ((u_i)_M, (v_i)_M, D)/((u_i)_M^2 + (v_i)_M^2 + D^2)^{1/2}$ is the unit vector that represents the direction from the focal spot (i.e., the origin of the xyz coordinate system) to the i-th image point in the "imaging" system.

The minimization of $\Sigma_i(d_i)^2$ can be achieved by use of a Procrustes algorithm (See, e.g., P. H. Schoeneman, "A generalized solution of the orthogonal Procrustes problem, "*Psychometrika* 31: 1–10, 1966; and P. H. Schoeneman, R. M. Carroll, "Fitting one matrix to another under choice of a central dilation and a rigid motion," *Psychometrika* 35: 245–254, 1970), which determines the translation, rotation, and scale factor that matches two n-dimensional configurations of points in the least squares sense. In the present system, n equals 3 because there are two 3D sets of points, i.e., $P_i$ and $(P_i)_p$. For the Procrustes algorithm, $P_i$ and $(P_i)_p$ are employed as the original and target configurations, respectively.

It should be noted that this application of the projection-Procrustes technique differs from that in the previous technique in that the model is not positioned with its center of mass at an arbitrary z location, i.e., D/2, because the object and its size are known in this application. Instead, it is positioned based on the calculated magnification of the object and the differences between the projections of the model and the actual image data. In addition, the calculated scaling is ignored because the size of the object is known. Thus, the projection-Procrustes technique is used only for determining the rotation required to align the points in the model with their respective projection lines.

(3) Iterative Refinement of the Alignment

When the Procrustes technique is applied, the rotation matrix and the translation vector relating $P_i$ and $(P_i)_p$ are calculated. If no rotation is required, i.e., if $P_i$ and $(P_i)_p$ are already optimally aligned, the rotation matrix returned by the Procrustes technique has zeros in the off-diagonal elements, $r_{12}$, $r_{13}$, and $r_{23}$. If small rotations are required, these off-diagonal elements represent misalignments and are subsequently used for refinement of the rotations applied to the object.

Starting with the estimate of the position and orientation of the model, an iterative process of refining the rotation matrix and the translation vector is begun. This refinement process proceeds in the following manner. The off-diagonal elements, $r_{12}$, $r_{13}$, and $r_{23}$, are monitored, and the best estimates of the rotation angles in the xy, xz, and yz planes ($\theta_{xy}$, $\theta_{xz}$, and $\theta_{yz}$, respectively) are stored. These angles are modified by the respective off-diagonal elements one at a time, i.e., first the xy rotation, etc. The model is then rotated by the rotation matrix generated by use of the modified angle. The projection-Procrustes technique is applied, and the respective off-diagonal element is compared with the previously calculated off-diagonal element. If the projection-Procrustes technique returns an off-diagonal element that is smaller than the previously calculated one, the algorithm assumes that the model is better aligned with the more recent adjustment than without it. The adjusted angle is therefore taken as a better estimate of the rotation in that plane.

The new respective off-diagonal element returned by the projection-Procrustes technique is then taken as the adjustment for the next iteration. This process continues for a given rotation axis until the angle returned by the projection-Procrustes technique is either greater than the adjustment angle or less than a predetermined threshold. Each of the three angles is refined individually in this iterative manner. After each angle has been refined in this way, the translation vector is refined as described above, by use of the model rotated by the refined angles. This sequence of steps is repeated forty times. At each of these forty iterations, the threshold for halting the iteration is reduced, i.e., the threshold is set to (maxangle/n)°, where maxangle is a variable that is usually set to 10, and n is the number of iterations. The number of iterations and maxangle could be changed. The primary aspects are that the threshold must start high, e.g., approximately 10–20 degrees, and be reduced gradually to a small threshold angle, e.g., 0.25 degrees. The manner in which this is done does not greatly affect the accuracy of the results.

Repetition of these steps is necessary because this process does not yield the desired result with a single iteration due to the coupling of the angles in the rotation matrix as well as their coupling with the estimates of the translation vector. In addition, the coupling of the angles affects the convergence of this approach when a single threshold was used. After one angle had been refined, it would be "readjusted" (often upward) during the refinement of a subsequent angle. By setting an initially rather high threshold and reducing it gradually, all angles appear to converge more or less at the same rate, and the upward readjustment is not as substantial because no one angle is refined more than the others. At the final iteration, the threshold angle is set to 0.25°, when maxangle is set to 10.

After these iterations, the model is rotated and shifted by the determined rotation matrix and translation vector. The discrepancies between the projected model data and the image data are calculated, and the rotation returned by the projection-Procrustes technique is displayed. The off-diagonal elements indicate residual errors in the angles of rotation about the respective axes. These are usually of the order of 0.01 degree.

There is more than one rotation matrix to which the technique can converge because the minimization of the off-diagonal elements in the rotation matrix alone is performed. The calculated configurations resulting from the inappropriate rotations are rotated 180° about one of the primary axes relative to the true configuration and yield large image error. Therefore, when two of the diagonal elements are approximately equal to −1, 180° is added to the calculated rotation about the appropriate axis, and the iterative refinement of the alignment is repeated.

3. Determination of the Geometry Using the Procrustes Technique

The position of the calibration object relative to the respective focal spots is calculated for each x-ray imaging system. Thus, two sets of points having coordinates defined relative to the focal spots in the respective imaging system are obtained. The equations describing relationship between these two sets of points are directly related to equation 1, relating the two x-ray imaging systems. Specifically, the rotation matrix, [R], and the translation vector, t, relating these two systems can be calculated by applying the Procrustes technique (See, e.g., P. H. Schoeneman, "A generalized solution of the orthogonal Procrustes problem," *Psychometrika* 31: 1–10, 1966; and P. H. Schoeneman, R. M. Carroll, "Fitting one matrix to another under choice of a central dilation and a rigid motion," *Psychometrika* 35: 245–254, 1970) to the two sets of points. The Procrustes technique determines the rotation, translation and scaling relating two sets of n-dimensional points in a least squares sense.

C. Identification of Electrode and Lead Centerline Positions in the Images

Knowing the image geometry from the above calculations allows for the accurate and precise identification of the lead in each of the image plane projections. The identification of the lead in each image requires identifying a plurality of discrete points along the centerline of the lead. The greater the number of centerline points identified, the greater the accuracy and precision of the calculated position. It is preferred to identify between about 20 and about 30 such positions. The initial identification of those centerline points is done manually. The individual performing the process manually indicates those 20 to 30 points on the first image projection. Identification of centerline points in all acquired images can be manually performed. However, automated means of identifying centerline points in subsequent images are preferred. Such automated means are well known in the art. By way of example, template matching (A. Kano, K.

Doi, H. MacMahon, D. D. Hasell, M. L. Giger: Digital image subtraction of temporally sequential chest images for detection of interval change. *Med. Phys.* 21: 453–461, 1994) and vessel tracking techniques (K. R. Hoffmann, K. Doi, H. P. Chan, L. Fencil, H. Fujita, A. Muraki: Automated tracking of the vascular tree in DSA images using a double-square-box region-of-search algorithm. *Proc SPIE* 626: 326–333, 1986 and K. R. Hoffmann, K. Doi, S.-H.Chen, H. P. Chan: Automated tracking and computer reproduction of vessels in DSA images. *Invest Radiol* 25: 1069–1075, 1990) can be employed to locate the lead and its centerline automatically in subsequent images.

After indication of the electrodes and the lead, a modification of the vascular region-growing technique (N. Alperin, K. R. Hoffmann, K. Doi, K. G. Chua: Automated analysis of coronary lesions from cineangiograms using vessel tracking and iterative deconvolution techniques. *Computers in Cardiology*Jerusalem, Israel, —Sep. 19–22, 1989, *Proc. IEEE*, 153–156, 1990) are employed to extract the electrodes from the background. The extracted electrode pixels are used as a template, and the electrodes in the next image in the sequence are determined using a cross-correlation technique (A. Kano, K. Doi, H. MacMahon, D. D. Hasell, M. L. Giger: Digital image subtraction of temporally sequential chest images for detection of interval change. *Med. Phys.* 21: 453–461, 1994).

After the electrodes have been located, the lead centerline is tracked using a modification of the double-square-box technique (K. R. Hoffmann, K. Doi, H. P. Chan, L. Fencil, H. Fujita, A. Muraki: Automated tracking of the vascular tree in DSA images using a double-square-box region-of-search algorithm. *Proc SPIE* 626: 326–333, 1986 and K. R. Hoffmann, K. Doi, S.-H. Chen, H. P. Chan: Automated tracking and computer reproduction of vessels in DSA images. *Invest Radiol* 25: 1069–1075, 1990). To ensure correct tracking of the lead in the presence of non-uniform background, the tracking algorithm can be modified to incorporate the shape of the lead in the previous image and the known continuity of the lead. After tracking, the tracking points is fit with smooth curve. A template of the electrodes in this new image is obtained, and the above described process is repeated for the next image in the sequence, and so on, until the electrodes and lead centerlines are identified in each of the images for that projection. These centerline points are then fitted by a spline curve, yielding approximately 100–300 points. The points and curve fit can be modified until satisfactory centerlines are obtained.

D. Temporal Interpolation of the Positions of Points Along the Pacemaker Lead As set forth above, biplane images of the lead in the subject are obtained alternately every 1/60th second during the entire imaging sequence, i.e., each imaging system acquires images every 1/30th of a second, alternating with the other system. Thus, each image is obtained at a different time (i.e., the images are non-synchronous). To determine the position of the lead in 3D throughout the heart cycle, this non-synchronicity is overcome using temporal interpolation, which is carried out as set forth below.

After the position of the centerline of the lead is determined for each image in the imaging sequence for both projections, corresponding points along the centerline of the lead are determined for each image. The positions of the corresponding points are then interpolated temporally so as to yield the position of each point along the lead at a given point in time. That given time point can be the time at which either of the images was acquired or any time in between those times. In a preferred embodiment, the time point is halfway between the two acquisitions for that projection. Thus, positions of lead centerlines are obtained that correspond to the positions at which the lead should have been at the time of acquisition by the other imaging system. Both polynomial (second-order, four points) and linear fitting (first-order, two points) of the temporal data are used, and both yield the same results to within the fluctuations in the temporal data.

In addition to allowing for determination of the pacemaker lead throughout the entire cardiac cycle, the temporal interpolation of data allows for self-diagnosis of the imaging calculations over time. This self-diagnosis can be accomplished by temporally interpolating two acquired images from the same image plane at different points in time (e.g., images acquired 2/30th of second apart). Those two acquired images are then interpolated to a time in between the acquisition times, which time corresponds to a third acquisition time (e.g., an image acquired 1/30th, 2/30th or 3/30ths of a second after the time of the first acquired image in that plane). The temporally derived image can then be directly compared to the actual image acquired at that time. Agreement between the temporally derived and actually acquired images indicates an accurate and precise functioning of the system.

The temporal interpolation of images comprises two steps: determination of correspondence of points along the lead centerline and temporal interpolation of the lead centerline data. Those steps are carried out as follows.

1. Determination of Correspondence of Points Along the Lead Centerline

The cumulative distance, d(j), along the length of the lead centerline (to be called arc length) from the junction of the lead and the electrode to a given point, j, on the lead is determined for the first image in the sequence as defined by Equation (8), below $$d_1(j) = \sum_{i=2}^{j} |u_1(i) - u_1(i-1)|, \qquad (8)$$

where the subscript 1 refers to the first image in the sequence, and the image coordinates of point i along the lead centerline are given by the vector u(i). For other images, I, in that sequence for that projection, points$_{j\ I}$, having the same arc length as a given point in the first image, i.e., $d_I(j') = d_{1\ (j)}$, are assumed to correspond. The points along the centerline are discrete and are separated by approximately 1 pixel. Therefore, if $d_{I\ (jI)}$ lay between two $d_{1\ (j)}$'s, linear interpolation is employed to estimate $u_{I\ (jI)}$. In this way, the position of each point on the lead centerline is determined as a function of time. It should be noted that the distance along the lead from the electrode to a given point on the lead depends on the angulation of the lead relative to the plane of the image intensifier (i.e., portions of the lead can be foreshortened, and this foreshortening varies with time as the lead moves relative to the intensifier). However, from one time point to the next, the change in angulation is likely be relatively small, except during systole. Thus, the error in correspondence between temporally adjacent images is expected to be small.

2. Temporal Interpolation of the Lead Centerline Data

With the position of each point on the lead determined as a function of time, the position of each point can be determined at arbitrary times, in particular, the time at which the acquisition for the other imaging system occurred. The set of temporal positions of each lead point in each projection is fitted independently using linear (first order, two points) and cubic (third order, four points) fits to the data. From these fits, the positions of all points on the lead in the first image set (AP—anterior-posterior) are calculated for those times that the second images (Lateral) were acquired, and vice versa. Both of these techniques were used, and both were found to yield basically the results equivalent to within the fluctuations in the temporal data. In addition, interpolation techniques based on a two-dimensional ellipsoid-based model can be used. The ellipsoid model may yield better results because of the almost cyclical nature of the heart beat.

The temporal interpolation method used here is one of many that can be applied. Critical is that an accurate temporal interpolation scheme must be applied so as to obtain "simultaneous" images of the pacemaker lead centerline.

E. Calculation of 3D Lead Positions

Subsequent to the determination of the position of the leads in each of the images and interpolation to the simultaneous time points, the corresponding points along the length of the leads in the two biplane images are determined by use of a technique based on epipolar lines (See, e.g.,.M. J. Potel, J. M. Rubin, S. A. MacKay, A. M. Aisen, J. Al-Sadir, and R. E. Sayre, "Methods for evaluating cardiac wall motion in three dimensions using bifurcation points of the coronary arterial tree," Invest Radiol 8: 47–57, 1983; and D. Parker, D. Pope, R. Van Bree, and H. Marshall, "Three-dimensional reconstruction of moving arterial beds from digital subtraction angiography," Comp and Biomed Res 20: 166–185, 1987). With the imaging geometry determined, the line that connects the focal spot and a point in one projection can be projected in the second projection (See FIG. 7). This projected line intersects the lead centerline appearing in that image. The point of intersection between the epipolar line and the lead centerline is taken to be the point in the second image that corresponds to the point in the first image. If there is more than one intersection, the point of intersection nearest to and with a greater arc length than the previous intersection point is taken as the corresponding point. A series of multiple intersections can occur when the epipolar line is parallel to the lead centerline. In this case, corresponding points are determined by linear interpolation between the points with only one intersection on either side of this region in which the centerline and epipolar line are parallel.

Figure 7:
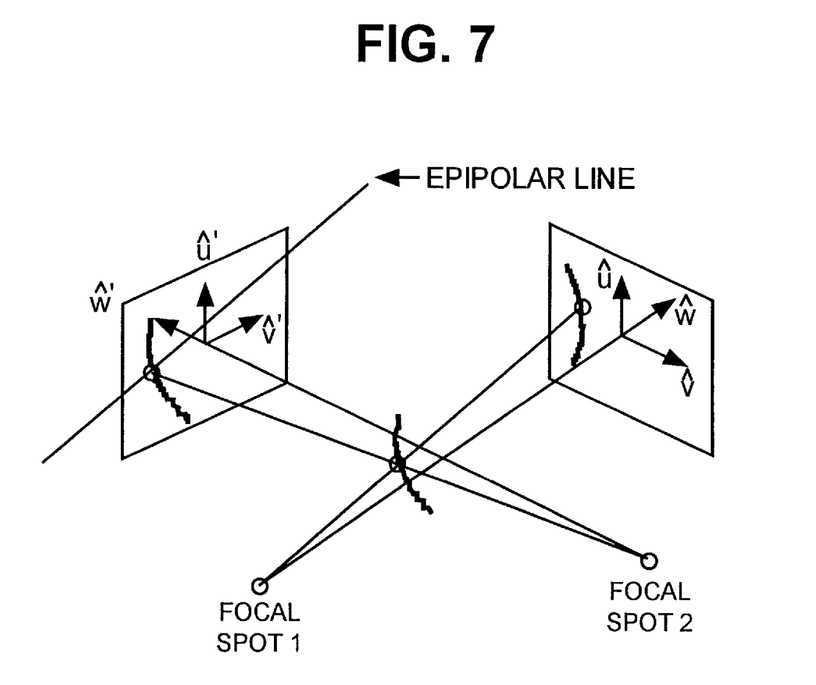
FIG. 7 shows the use of epipolar lines to determine three-dimensional location.

With the corresponding points identified along the entire length of the lead in the two images, the calculated imaging geometry is used to determine the 3D position of those points that generated the corresponding points in the two images. In the analysis, errors in the calculated geometry propagate into improper correspondences for which the primary effect is to change the position of the lead. The secondary effect is to change the shape of the lead. To evaluate possible sensitivity to errors in the calculated geometry, the correspondence is established by use of the epipolar line technique for the two geometries calculated from the two cube positions.

A technique similar to that set forth above can be used to calculate the 3D location of the pacemaker electrodes. For the evaluation of the electrode positions, the end points of the centerline of the electrodes are chosen because they can be identified uniquely in each biplane image. The edges of the electrodes as seen in the two biplane images do not correspond, and therefore they are not used. The identified end points, however, are known to correspond. Their positions are interpolated temporally as described above, and the 3D positions are calculated based on the calculated imaging geometries.

II. Accuracy and Precision of the Process

The process of the present invention provides accurate and precise three-dimensional location data. Furthermore, the process allows for the monitoring and correction of errors during data generation. By way of example, the accuracy and precision of the temporal interpolation step can be monitored by the appropriate selection of image times and image planes (See above). As also set forth above, the accuracy and precision of calculating the imaging geometry (e.g., the values of [R] and t) can be enhanced by acquiring a plurality of images of the calibration object in different orientations.

As is known in the art, the overall accuracy and precision of a process are a function of the errors attendant to each step and the propagation of those errors throughout the process. Each component of the process can be evaluated for its accuracy and/or precision.

A. Evaluation of the Precision of the Calculated Imaging Geometry and Calculated 3D Positions For each patient acquisition, the imaging geometry is determined as described above. The calculated geometries are evaluated by placing the calibration object (e.g., cube) at three distinct positions relative to the imaging system, acquiring images for each of these positions, and calculating the geometry for each of these positions. For each of the three cube positions, the rotation matrices and translation vectors relating the two imaging systems are calculated. The imaging geometries calculated from the two cube positions are compared in two ways.

First, the calculated rotation matrices [R] and translation vectors (t) defining the biplane imaging geometry are calculated for each cube position and compared. For t, the mean differences in the x, y, and z components of the translation vector, t, are compared. The difference between the rotation matrices, $R_1$ and $R_2$, calculated for the respective two cube positions, is characterized by the angle relating the two rotation matrices and is given by Equation (9), below $$E_R = \cos^{-1}[(Tr\ \{[R_1^T R_2]\}-1)/2]. \tag{9}$$

Second, the precision of the 3D positions calculated using the three calculated imaging geometries is evaluated as follows. The 3D positions of the lead beads are calculated using the image data obtained for the one cube position and each of the three calculated imaging geometries. The difference in the 3D positions (x, y, z and magnitude) in these data sets is calculated. This process is repeated for the images obtained with the other cube positions. The difference in the 3D positions can be taken as a direct indicator of the precision of the final 3D lead positions.

B. Evaluation of the Indicated and Calculated Centerlines

To evaluate the reliability of the centerline calculations, the centerlines generated by two observers and the subsequent temporal tracking and interpolation of the centerline are compared. The corresponding points can be determined by a variety of means known in the art. By way of example, use of the cumulative arc length as described above, and the Euclidean distance between the corresponding points is calculated by use of all corresponding points along the lead. The average of these distances is also calculated.

C. Evaluation of the Precision of the Temporal Interpolation Data

To evaluate the quality of the interpolated data, the electrode points and lead centerline data obtained from sets of images separated by $\frac{1}{15}$th of a second are used to interpolate the data for the frame in between for each projection. These interpolated data are then compared with the actually acquired data for that time point. The corresponding points along the lead are determined using the cumulative arclength as described above. The distance along x, y axes and the Euclidean distance between the corresponding points are calculated for all corresponding points along the lead. For a given projection, these data are assembled into 3D data sets having axes of time, cumulative arclength, and distance, for rendering and analysis (data sets I). For comparison, these distances are calculated between corresponding points for images acquired adjacently in time, i.e., separated by $\frac{1}{30}$th sec. These data are also assembled into 3D data sets (data sets II). The data I are divided by the data II on a point by point basis to yield distance errors relative to distance moved between frames. These data are used to estimate the temporal and spatial trends in the error in the temporal interpolation and used to evaluate improvements in the technique. In preliminary studies, the interpolation errors using frames separated by $\frac{1}{15}$th second are approximately one-half the amount the lead moves in $\frac{1}{30}$th of a second. Thus, the actual interpolation errors should be approximately $\frac{1}{4}$th the amount the lead moves from frame to frame.

D. Evaluation of Effect of Errors in Correspondence on Calculated 3D Positions In the analysis, errors in the geometry and temporal interpolation propagate into improper correspondences along the length of the lead for which the primary effect is to change the position of the lead. The secondary effect is to change the shape of the lead. To evaluate possible sensitivity of the 3D lead centerline to errors in the geometry, the epipolar line correspondence is performed for the three imaging geometries calculated using the three cube positions. The difference in the 3D positions (x, y, z and magnitude) between these data sets are calculated for corresponding points along the length of the lead at each point in time. Points with the same cumulative arclength (calculated in 3D) are taken to correspond. These differences indicate primarily an incorrect positioning of the lead. As an indicator of the error in the shape of the lead, the standard deviation of these quantities along the length of the lead is also determined. The effect of the temporal interpolation on the 3D lead positions is evaluated by applying the epipolar line technique to the image data calculated using the three interpolation schemes as well as image data without temporal interpolation. The correspondence and distance measures is calculated as for the geometry evaluation. In addition, the distance measures calculated from the interpolated data is divided by the distance measures calculated from the non-interpolated data to obtain relative distance errors.

The Examples to follow illustrate preferred embodiments of the present invention and are not limiting of the specification or claims in any way.

EXAMPLE 1

Clinical System for Use in a Cardiac Catheterization Suite

The following is a description of a clinically usable system for using the process of the present invention in the catherization laboratory. A user interface, which is easy to use and provides the necessary information (e.g., calculated stresses and their reliability, and the proper clinical protocols ) are key elements of this transfer.

A clinically usable system will be easy to use and easy to place in catheterization laboratories. While digital acquisition is becoming more prevalent in catheterization laboratories, the immediate access to the clinical data is still not common. Thus, the image data is captured when played back on a standard catheterization lab monitor using off-the-shelf frame-grabbing technology. Direct digital data can also be used. To ensure that the developed interface is useable on any platform subsequent to image capture, the user interface is based on Xwindows and Motif which are the standards for interfaces on Unix-based computers today. Conversion to other graphics interfaces such as WindowsNT or Windows95, in the future, the interface can be developed so as to require nominal input, as described below.

After the images are resident on the computer, the images of the calibration object is displayed automatically. The user is prompted to indicate the positions of the lead beads which correspond to an ordered labeling of those beads in one projection and then the other. The protocol calls for use of two or more positions of the calibration phantom to check further the reliability of the calculated geometry for the particular patient. The user thus has to input points for a total of four images of the calibration phantom. The user is then prompted to enter the orientation information for each of the biplane imaging systems. Although this information is less accurate than the geometry calculated by the techniques described above, they can be used to check the calculated geometry for gross errors. Subsequent to the indication of the points, a background job is initiated to determine the imaging geometry.

The first image of the lead for each projection is then presented to the user. The user is asked to indicate the most distal point of the first electrode, its more proximal end, the most distal point of the second electrode, its more proximal end, and a few additional points are indicated along the length of the lead centerline with one of these points placed at the end of the lead to be tracked. These points serve as the starting points of the analysis to determine the electrode and lead centerline positions as a function of time (see above). Once the centerlines have been indicated, a second background job is initiated in which the rest of the calculations proceeds automatically.

After the completion of the manual indication of the lead centerlines, the results of the geometry calculations are then displayed. These results include the calculated rotation matrix and translation vector for each position of the calibration phantom, the final errors for each projection, the differences between these calculated quantities, and the differences between the 3D positions of the calibration phantom using the three calculated geometries. The user then indicates whether the geometries are acceptable, an average of the translation vectors and the rotation matrix which lies halfway between the calculated rotations is calculated and stored. If the user indicates that the geometries are unacceptable, he is presented with each of the images of the calibration phantom again for a second indication of the points in the images. In our experience, points had to be reindicated only when improper correspondence was indicated which happened infrequently.

After the electrode and lead centerline positions have been calculated as a function of time and the user has accepted the calculated geometry, the user is presented with a temporal sequence for each projection, in which the positions of the determined centerlines are displayed. If the centerline in a particular image is acceptable, the user need only go to the next image. If it is unacceptable, the user is allowed to change points along the centerline. The centerline is refit, and the user repeats these last few steps until an acceptable centerline is determined for that image, after which the user goes to the next image in the sequence. These steps are repeated for each image sequence.

The positions of the lead centerlines are then interpolated temporally using linear, cubic, and ellipsoidal techniques. The frame-to-frame motion and the difference between calculated and centerlines from acquired images are calculated for each image in the sequence, i.e., throughout the heart cycle, and their results are displayed in a graph format along with the calculated average errors for each technique. The user is then prompted as to which temporal interpolation results to use.

The calculated imaging geometry and the interpolated centerlines are used in the epipolar line program in which the 3D positions of the lead centerline are determined. The calculated 3D positions of the lead are then displayed as a cine-loop, during which the user is able to rotate the 3D centerline to view it from arbitrary projections. The user then indicate whether the calculated centerlines are acceptable or not. If they are not acceptable, the user is prompted as to the modification of the geometry requested. After the modification, the 3D results is again displayed. If the calculated 3D centerline is acceptable, the user indicates this and the stress along the length of the lead as a function of time as well as the reliability of the stresses is calculated.

What is claimed is:

1. A process of determining the three dimensional location of a pacemaker lead in a subject's heart throughout the cardiac cycle the process comprising the steps of:
   (a) acquiring a plurality of two-dimensional images of the lead;
   (b) calculating the imaging geometry;
   (c) identifying the two-dimensional position of the lead in each of the images;
   (d) temporally interpolating the identified two-dimensional positions to identify a two-dimensional position at a single time; and
   (e) calculating the three dimensional location of the lead from the two-dimensional position at that time.

2. The process of claim 1 wherein acquiring the images is accomplished using a biplanar imaging system having a first focal point at a first distance from a first imaging plane and a second focal point located at a second distance from a second imaging plane, wherein the subject heart is placed between the first focal point and the first imaging plane and between the second focal point and the second imaging plane.

3. The process of claim 2 wherein images of the lead are obtained alternately in each plane over the duration of at least one complete cardiac cycle.

4. The process of claim 2 wherein an image of the lead is generated every $\frac{1}{60}$th of a second throughout the cardiac cycle.

5. The process of claim 2 wherein neither the first nor the second imaging plane is perpendicular to the plane of the pacemaker lead.

6. The process of claim 2 wherein one of the first and the second imaging planes is parallel to the plane of the pacemaker lead.

7. The process of claim 2 wherein the first imaging plane is oriented at an angle of between 30 degrees and 150 degrees to the second imaging plane.

8. The process of claim 7 wherein the first imaging plane is oriented at an angle of between 60 degrees and 120 degrees to the second imaging plane.

9. The process of claim 2 wherein the position of the lead is determined by identifying in each image a centerline of the lead by indicating a plurality of points along the length of the lead.

10. The process of claim 9 wherein between about 20 and about 30 points are indicated.

11. The process of claim 9 wherein the position of points along the centerline is indicated as a function of a single time.

12. A process for determining the precision of the process of claim 11 comprising at least one of the following steps:
   (a) calculating a plurality of imaging geometries by generating a plurality of images of the claibration object;
   (b) precisely identifying the centerline of the lead using arclengths measured from a junction of the lead and an electrode component of the pacemaker;
   (c) calculating accuracy and precision of temporal interpolation using reduced frame rate data and correspondences along the length of the lead;
   (d) identifying a plurality of centerlines of the lead using a plurality of image geometry calculations and calculating precision of the plurality of centerlines with established correspondences obtained using arclengths measured from a junction of the lead and an electrode component of the pacemaker.

13. The process of claim 1 wherein the imaging geometry is calculated by acquiring at least one image of a calibration object and calculating the geometry from that image using a single projection point analysis, wherein the calibration object contains at least four imageable points in at least two different planes.

14. The process of claim 13 wherein two images of the calibration object in different orientations are acquired.

15. The process of claim 1 wherein the single time is the time at which any one image was obtained.

16. The process of claim 1 wherein the three-dimensional location of the lead is calculated using epipolar techniques.

* * * * *

UNITED STATES PATENT AND TRADEMARK OFFICE
CERTIFICATE OF CORRECTION

PATENT NO. : 5,859,922

DATED : January 12, 1999

INVENTOR(S): Kenneth R. Hoffmann

It is hereby certified that error appear(s) in the above-identified patent and that said Letters Patent are hereby corrected as shown below:

Column 1, Line 10, after "subject." please insert -- The United States Government may have certain rights in the present invention pursuant to Grant No. NIH CA47043.--

Column 6, Line 46, please change "$(x'_i, y''_i, z''_i)$" to -- $(x'_i, y'_i, z'_i)$.

Column 14, Line 46, please change "points,$_{jI}$," to -- points, j I,--.

Signed and Sealed this

Twenty-second Day of May, 2001

Attest:

NICHOLAS P. GODICI

*Attesting Officer*   *Acting Director of the United States Patent and Trademark Office*